(12) United States Patent
Wang et al.

(10) Patent No.: US 11,583,180 B2
(45) Date of Patent: Feb. 21, 2023

(54) OPTICAL COMPONENT FOR RETINAL IMAGING AND RETINA IMAGING DEVICE

(71) Applicants: REYEMICO (HANGZHOU) MEDICAL TECHNOLOGY LTD., Zhejiang (CN); Qingyang Wang, Zhejiang (CN)

(72) Inventors: Qingyang Wang, Zhejiang (CN); Guohua Shi, Zhejiang (CN)

(73) Assignees: Qingyang Wang, Zhejiang (CN); REYEMICO (HANGZHOU) MEDICAL TECHNOLOGY LTD., Zhejiang (CN)

( * ) Notice: Subject to any disclaimer, the term of this patent is extended or adjusted under 35 U.S.C. 154(b) by 916 days.

(21) Appl. No.: 16/471,846

(22) PCT Filed: Dec. 14, 2017

(86) PCT No.: PCT/CN2017/116197
§ 371 (c)(1),
(2) Date: Feb. 12, 2020

(87) PCT Pub. No.: WO2018/113585
PCT Pub. Date: Jun. 28, 2018

(65) Prior Publication Data
US 2020/0214558 A1      Jul. 9, 2020

(30) Foreign Application Priority Data

Dec. 20, 2016   (CN) .......................... 201611182890.8

(51) Int. Cl.
*A61B 3/10* (2006.01)
*A61B 3/12* (2006.01)
*A61B 3/14* (2006.01)

(52) U.S. Cl.
CPC .............. *A61B 3/1025* (2013.01); *A61B 3/12* (2013.01); *A61B 3/14* (2013.01)

(58) Field of Classification Search
CPC ............ A61B 3/1025; A61B 3/12; A61B 3/14
(Continued)

(56) References Cited

U.S. PATENT DOCUMENTS

2005/0012899 A1   1/2005   Ferguson
2006/0132711 A1   6/2006   Iwanaga
(Continued)

FOREIGN PATENT DOCUMENTS

CN   101292859   10/2008
CN   101862178   10/2010
(Continued)

OTHER PUBLICATIONS

Final Office Action dated Oct. 5, 2021.
(Continued)

*Primary Examiner* — Mohammed A Hasan
(74) *Attorney, Agent, or Firm* — Ipsilon USA, LLP (57) ABSTRACT

The disclosure provides an optical component for retinal imaging including: a light source module, a beam splitter, an imaging module, a scanning module, and a flat field objective lens. The flat field objective lens is between the scanning module and a detection position, the light source module is configured to emit, to the beam splitter, a detection light for illuminating a fundus, the detection light being guided by the beam splitter to the scanning module and emitted to the detection position through the scanning module and the flat field objective lens, reflected light from the detection position can pass through the scanning module and reaches the beam splitter, and is guided by the beam splitter to the imaging module. The scanning module includes a scanning objective lens reciprocally movable along its central axis, (Continued)

and the flat field objective lens is reciprocally movable along its central axis.

19 Claims, 4 Drawing Sheets

(58) Field of Classification Search
USPC ........................................................ 351/221
See application file for complete search history.

(56) References Cited

U.S. PATENT DOCUMENTS

| | | | | |
|---|---|---|---|---|
| 2010/0128221 | A1* | 5/2010 | Muller | A61B 3/1025 |
| | | | | 348/78 |
| 2013/0016993 | A1 | 1/2013 | Akamatsu | |
| 2013/0169931 | A1 | 7/2013 | Lee et al. | |
| 2013/0278631 | A1* | 10/2013 | Border | G06Q 30/02 |
| | | | | 345/633 |
| 2016/0327779 | A1* | 11/2016 | Hillman | G02B 23/04 |
| 2021/0121063 | A1* | 4/2021 | Shi | A61B 3/1225 |

FOREIGN PATENT DOCUMENTS

| | | |
|---|---|---|
| CN | 102008288 | 4/2011 |
| CN | 102429634 | 5/2012 |
| CN | 103181749 | 7/2013 |
| CN | 103750814 | 4/2014 |
| CN | 103989453 | 8/2014 |
| CN | 204105944 | 1/2015 |
| CN | 104640497 | 5/2015 |
| CN | 104783755 | 7/2015 |
| CN | 105534473 | 5/2016 |
| CN | 107126189 | 9/2017 |
| JP | 2013-144236 | 7/2013 |
| JP | 2013144236 | 7/2013 |
| JP | 2013-208394 | 10/2013 |
| JP | 2013208394 | 10/2013 |
| JP | 2014028319 | 2/2014 |
| JP | 2015-085044 | 5/2015 |
| JP | 2015085044 | 5/2015 |

OTHER PUBLICATIONS

JP Office Action dated Feb. 2, 2021.
CN Office Action dated Jun. 22, 2018.
Indian Examination Report dated Jan. 29, 2021.
CN Office Action dated Nov. 5, 2018.
Japenese Office Action dated Jul. 21, 2020.
Chinese Office Action dated Jul. 21, 2020.
International Search Report dated Feb. 23, 2018.

* cited by examiner

```
                    ┌─────────────────────────────────────────────────────────┐
                    │  placing head of subject on the head frame, turning on  │
                    │  the annular light source, adjusting the position of    │── S1
                    │  the head frame such that light emitted by the annular  │
                    │  light source illuminates the cornea of the human eye   │
                    └─────────────────────────────────────────────────────────┘
                                             │
                                             ▼
              ┌───────────────────────────────────────────────────────────────┐
              │  focusing light reflected back from the cornea of the human   │
              │  eye and traveling along the optical path into the area array │
              │  photodetector to realize real-time monitoring of the pupil   │── S2
              │  of the human eye, and determining that the human eye has     │
              │  been adjusted to a center position of the optical path if    │
              │  the pupil is located in the middle of the imaging field      │
              └───────────────────────────────────────────────────────────────┘
                                             │
                                             ▼
          ┌────────────────────────────────────────────────────────────────────┐
          │  turning on the point light source, turning on the galvanometer    │
          │  scanner, turning on the control processor formed by the function  │
          │  generator board, the image acquisition board, and the main        │
          │  control computer, and for the defocusing amount of a refractive   │── S3
          │  error of the human eye, driving the flat field objective lens to  │
          │  generate a defocusing compensation amount along the second guide  │
          │  rail to compensate for the defocusing amount of the human eye    │
          └────────────────────────────────────────────────────────────────────┘
                                             │
                                             ▼
                  ┌──────────────────────────────────────────────────────┐
                  │  letting the subject keep the eye stable, and        │── S4
                  │  starting a data acquisition program for video       │
                  │  acquisition                                         │
                  └──────────────────────────────────────────────────────┘
                                             │
                                             ▼
              ┌──────────────────────────────────────────────────────────────┐
              │  turning on a corresponding LED of the light-emitting array   │
              │  by the control processor according to an area of the retina  │── S5
              │  to be imaged, to illuminate the area of the retina           │
              └──────────────────────────────────────────────────────────────┘
                                             │
                                             ▼
            ┌─────────────────────────────────────────────────────────────────┐
            │  causing the scanning objective lens to generate defocus along  │
            │  the first guide rail to illuminate layers of the retina at     │── S6
            │  different depths, thereby acquiring a three-dimensional image  │
            │  of the layers of the retina at different depths                │
            └─────────────────────────────────────────────────────────────────┘
```

OPTICAL COMPONENT FOR RETINAL IMAGING AND RETINA IMAGING DEVICE

RELATED APPLICATION

This application is a National Phase of PCT/CN2017/116197, filed on Dec. 14, 2017, which claims the benefit of priority from Chinese Patent Application No. 201611182890.8, filed on Dec. 20, 2016, the entirety of which are incorporated by reference.

TECHNICAL FIELD

The present disclosure relates to the field of medical devices, and in particular relates to an optical component for retinal imaging and a retina imaging device including the same.

BACKGROUND

A retinal image of a human eye is indispensable information in diagnoses and treatments in ophthalmology, and tracking a change in morphology of a retina at the fundus in real time will help early diagnosis and prevention of physical diseases. R. H. Webb applies confocal scanning technique in living human retinal imaging, and a confocal vacuum pinhole at a side of a detector is configured to block out-of-focus stray light in a sample, so as to obtain a high-resolution image of a focal plane in the sample. However, scanning electric distribution adopted in the confocal technique is dispersed, resulting in low resolution, in the meanwhile, a light spot has low energy, and a weak light detector is used, resulting in slow imaging speed and acquired image having low contrast.

In order to solve the above problem, a confocal imaging device based on line scanning has appeared. However, the current confocal imaging device can only obtain a plan view of a retina, and stereoscopic detection of a retina cannot be achieved.

Therefore, how to realize stereoscopic detection of a retina has become an urgent technical problem to be solved in the art.

SUMMARY

An object of the present disclosure is to provide an optical component for retinal imaging and a retinal imaging device including the optical component, and a stereoscopic image of a retina can be obtained by using the retinal imaging device.

In order to achieve the above object, as an aspect of the present disclosure, there is provided an optical component for retinal imaging including: a light source module, a beam splitter, an imaging module, a scanning module, and a flat field objective lens, wherein the flat field objective lens is disposed between the scanning module and a detection position, the light source module is configured to emit, to the beam splitter, a detection light for illuminating a fundus, the detection light being guided by the beam splitter to the scanning module and emitted to the detection position through the scanning module and the flat field objective lens, reflected light from the detection position is able to pass through the scanning module and reaches the beam splitter, and is guided by the beam splitter to the imaging module, wherein the scanning module includes a scanning objective lens reciprocally movable along a central axis of the scanning objective lens, and the flat field objective lens is reciprocally movable along a central axis of the flat field objective lens.

Preferably, the scanning module includes a first guide rail extending in a direction coinciding with the central axis of the scanning objective lens, and the scanning objective lens is slidably disposed on the first guide rail.

Preferably, the optical component includes a second guide rail extending in a direction coinciding with the central axis of the flat field objective lens, and the flat field objective lens is slidably disposed on the second guide rail.

Preferably, the optical component further includes a first cylindrical lens disposed between the beam splitter and the scanning module and configured to convert a beam passing through the beam splitter into a linear beam and cause the linear beam to be emitted to the scanning module.

Preferably, the light source module includes a broadband point light source, a collimating lens and a first filter group arranged in sequence, the broadband point light source is configured to emit broadband lasers having a plurality of wavelengths, the first filter group includes a plurality of first filters, a number of the first filters being equal to a number of the plurality of wavelengths of the lasers emitted by the broadband point light source, wherein the first filters are capable of filtering the lasers emitted from the broadband point light source into lasers each having a predetermined wavelength, and each of the plurality of first filters is detachably disposed in an optical path of the optical component; and the imaging module includes a first imaging objective lens and a second filter group, the second filter group is disposed between the beam splitter and the first imaging objective lens such that light reflected by the beam splitter enters the first imaging objective lens after passing through the second filter group, the second filter group includes a plurality of second filters, and the plurality of the second filters are capable of transmitting fluorescence having different wavelengths, respectively.

Preferably, the light source module includes a first turntable, the first turntable is provided thereon with a plurality of first filter through holes in one-to-one correspondence with the plurality of first filters, and each of the plurality of first filters is disposed in a corresponding one of the plurality of first filter through holes.

Preferably, the imaging module includes a second turntable, the second turntable is provided thereon with a plurality of second filter through holes in one-to-one correspondence with the plurality of second filters, and each of the plurality of second filters is disposed in a corresponding one of the plurality of second filter through holes.

Preferably, the broadband point light source includes an argon laser emitter and a semiconductor laser emitter, the argon laser emitter being capable of emitting a broadband laser having a central wavelength of 488 nm and a broadband laser having a central wavelength of 514 nm, and the semiconductor laser emitter being capable of emitting a broadband laser having a central wavelength of 795 nm and a broadband laser having a central wavelength of 830 nm;

the first filter group includes a first filter capable of transmitting a laser having a wavelength of 488 nm, a first filter capable of transmitting a laser having a wavelength of 514 nm, a first filter capable of transmitting a laser having a wavelength of 795 nm, and, a first filter capable of transmitting a laser having a wavelength of 830 nm; and the second filter group includes a second filter capable of transmitting fluorescence having a wavelength of 500 nm and a second filter capable of transmitting fluorescence having a wavelength of 810 nm.

Preferably, the scanning module further includes a galvanometer scanner and a first dichroic beamsplitter, wherein the first dichroic beamsplitter and the scanning objective lens are sequentially arranged between the galvanometer scanner and the flat field objective lens; and the optical component further includes a test-object module including a light-emitting array and a third imaging objective lens, the light-emitting array including a plurality of light-emitting elements which are independently controllable, light emitted by any one of the light-emitting elements is capable of being emitted into the third imaging objective lens, directed to the first dichroic beamsplitter after being focused by the third imaging objective lens and reflected by the first dichroic beamsplitter to the flat field objective lens.

Preferably, the optical component further includes a pupil detection module, wherein the pupil detection module includes a second dichroic beamsplitter, an annular light source and a second imaging objective lens, and the annular light source has a hollow portion capable of transmitting light, and the second dichroic beamsplitter is disposed between the first dichroic beamsplitter and the third imaging objective lens such that light passing through the third imaging objective lens is able to pass through the second dichroic beamsplitter, the annular light source is disposed between the flat field objective lens and the detection position, the annular light source is able to emit light toward the detection position, light emitted by the light source module is able to pass through the hollow portion of the annular light source, light reflected from the detection position is able to be emitted to the first dichroic beamsplitter after passing through the hollow portion of the annular light source and reflected by the first dichroic beamsplitter to the second dichroic beamsplitter, and the second dichroic beamsplitter is able to reflect the light reflected by the first dichroic beamsplitter to the second imaging objective lens.

Preferably, the pupil detection module further includes an area array photodetector configured to receive light emitted from the second imaging objective lens.

Preferably, a transmissivity of the second dichroic beamsplitter is smaller than a reflectivity of the second dichroic beamsplitter.

Preferably, the imaging module further includes a second cylindrical lens, a slit aperture and a linear array photodetector which are arranged in sequence on a light exiting side of the first imaging objective lens, wherein the slit aperture, the light source module and the detection position are at conjugate positions.

Preferably, the slit aperture has a slit whose width is equal to Airy disk diameter of the first imaging objective lens.

Preferably, the beam splitter is disposed between the light source module and the scanning module such that light emitted by the light source module is able to pass through the beam splitter and reach the scanning module, the beam splitter is able to reflect reflected light from the detection position to the imaging module, the scanning module and the flat field objective lens are arranged on a first straight line, the imaging module is disposed on a second straight line perpendicular to the first straight line such that detection light emitted by the light source module is able to pass through the beam splitter, and reflected light from the detection position is able to be reflected by the beam splitter to the imaging module.

Preferably, the beam splitter includes a first light reflection portion and a first light transmission portion formed on the first light reflection portion, the first light reflection portion has a reflection surface facing the scanning module, the detection light emitted by the light source module is able to pass through the first light transmission portion, and the reflected light from the detection position is able to be reflected by the first light reflection portion to the imaging module.

Preferably, the beam splitter includes a transparent body and a beam splitting film disposed on the transparent body.

Preferably, the beam splitter is disposed between the imaging module and the scanning module, the imaging module, the beam splitter, the scanning module and the flat field objective lens are arranged on a third straight line, the light source module is disposed on a fourth straight line perpendicular to the third straight line such that detection light emitted by the light source module is able to be emitted onto the beam splitter and reflected by the beam splitter to the scanning module, and reflected light from the detection position is able to pass through the beam splitter to reach the imaging module.

Preferably, the beam splitter includes a second light reflection portion and a second light transmission portion, the second light reflection portion has a reflection surface facing the scanning module, the detection light emitted by the light source module is able to be emitted onto the second light reflection portion and reflected by the second light reflection portion to the scanning module, and the reflected light from the detection position is able to pass through the second light transmission portion to reach the imaging module.

Preferably, the beam splitter includes a transparent body and a beam splitting film disposed on the transparent body.

As another aspect of the present disclosure, there is provided a retina imaging device including an optical component and a processor, the optical component is the above optical component provided by the present disclosure, and the processor includes an image generation module configured to generate a corresponding image according to the light emitted from the imaging module.

Preferably, the optical component includes a second imaging objective lens, and the image generation module is further configured to generate a corresponding image according to light emitted from the second imaging objective lens.

Since eyes of most people are ametropic, the flat field objective lens in the optical component of the present disclosure reciprocates along the central axis of the flat field objective lens to generate different refractive compensation amounts, and therefore, defocusing amounts for refractive errors of different human eyes can be compensated for, and a clear human retinal image can be obtained by using the optical component provided by the present disclosure.

The retina is a layer having a thickness of about 300 μm at the fundus of the human eye and including multiple layers such as nerve fiber layer, nerve cell layer, blood vessel layer, visual cell layer and retinal pigment epithelium layer. Different diseases and physiological processes can be manifested on different layers of the retina. The scanning objective lens can reciprocate along its central axis, so as to generate different defocusing amounts. Under different defocusing amounts, images of layers of the retina at different depths can be observed, that is, the scanning objective lens can transmit light emitted from the layers of the retina at different depths to the imaging module, and images of different layers of the retina are obtained through the imaging module.

The optical component provided by the present disclosure can perform longitudinal tomography on the retina, obtain a three-dimensional image of the retina, and observe images of different layers of the retina, thereby improving the accuracy and comprehensiveness of clinical examination.

BRIEF DESCRIPTION OF THE DRAWINGS

Accompanying drawings, which constitute a part of the specification, are intended to provide a further understanding of the present disclosure, and are used for explaining the present disclosure together with the following specific implementations, rather than limiting the present disclosure. In the drawings:

FIG. 5 is a flow chart of a method of detecting a retina using a retina imaging device provided by the present disclosure.

DETAILED DESCRIPTION

The specific implementations of the present disclosure will be described in detail below with reference to the accompanying drawings. It should be understood that the specific implementations described herein are merely for the purpose of describing and explaining the present disclosure, rather than limiting the present disclosure.

Figure 1:
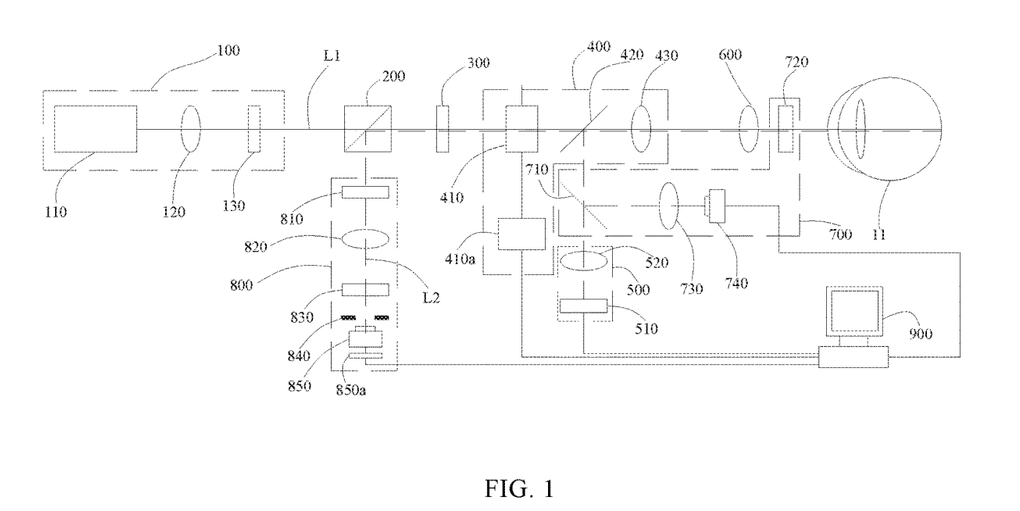
FIG. 1 is a schematic structural diagram of a first implementation of an optical component for retinal imaging provided by the present disclosure.

As shown in FIG. 1, as an aspect of the present disclosure, an optical component for retinal imaging is provided. The optical component includes a light source module 100, a beam splitter 200, an imaging module 800, a scanning module 400, and a flat field objective lens 600. The flat field objective lens 600 is disposed between the scanning module 400 and a detection position. It should be noted that a human eye 11 is located at the detection position.

The light source module 100 is configured to emit detection light (the detection light is a narrow beam) that illuminates the detection position, and the detection light is guided by the beam splitter 200 to the scanning module 400 and emitted to the detection position through the scanning module 400 to illuminate the detection position, i.e., the fundus of the human eye 11. Reflected light from the fundus of the human eye 11 can pass through the scanning module 400 to reach the beam splitter 200 and be guided by the beam splitter 200 to the imaging module 800. The scanning module 400 includes a scanning objective lens 430 that is reciprocally movable along a central axis of the scanning objective lens 430, and the flat field objective lens 600 is reciprocally movable along a central axis of the flat field objective lens 600.

It should be noted that the expression "guided by the beam splitter" herein includes at least two cases, one of which means passing through the beam splitter and the other of which means being reflected by the beam splitter. These two cases will be described in detail below, and will not be described here.

When imaging a subject's retina by using the optical component, an eye of the subject to be detected is located at the detection position, and the human eye 11 to be detected, the scanning objective lens 430, and the beam splitter 200 are all on a same straight line. When testing the subject, the light source module 100 is turned on to generate detection light. The detection light reaches the human eye 11 after passing through the beam splitter 200 and the scanning objective lens 430 of the scanning module 400. Light reflected by the retina at the fundus of the human eye can reach the beam splitter 200 after passing through the scanning objective lens 430, and is guided by the beam splitter 200 to the imaging module 800, and an image of the retina can be obtained by collecting light passing through the imaging module 800.

Since eyes of most people are ametropic, the flat field objective lens 600 in the optical component of the present disclosure reciprocates along the central axis of the flat field objective lens 600, so that different refractive compensation amounts can be generated, therefore, defocusing amounts for refractive errors of different human eyes can be compensated for, and a clear human retinal image can be obtained by using the optical component provided by the present disclosure.

The retina is a layer having a thickness of about 300 μm at the fundus of the human eye and including multiple layers such as nerve fiber layer, nerve cell layer, blood vessel layer, visual cell layer and retinal pigment epithelium layer. Different diseases and physiological processes can be manifested on different layers of the retina. The scanning objective lens 430 can reciprocate along its central axis, so as to generate different defocusing amounts, so that images of layers of the retina at different depths can be observed, that is, the scanning objective lens 430 can transmit light emitted from the layers of the retina at different depths to the imaging module 800, and images of different layers of the retina are obtained through the imaging module.

Specifically, by adjusting the defocusing amount of the scanning objective lens 430, images of the nerve fiber layer, the nerve cell layer, the blood vessel layer, the visual cell layer, and the retinal pigment epithelium layer can be obtained, respectively. By using the optical component provided by the present disclosure, longitudinal tomography can be performed on the retina, a three-dimensional image of the retina can be obtained, and images of different layers of the retina can be observed, thereby improving the accuracy and comprehensiveness of clinical examination.

For example, in the optical component provided by the present disclosure, when the defocusing amount of the scanning objective lens 430 is 0, an image of the blood vessel layer can be obtained; when the defocusing amount of the scanning objective lens 430 is −100 μm, an image of the nerve fiber layer can be obtained; and when the defocusing amount of the scanning objective lens 430 is 100 μm, an image of the cell layer can be obtained.

In the present disclosure, the positional relationship among the beam splitter 200, the light source module 100, the imaging module 800 and the scanning module 400 is not particularly limited.

For example, in the implementation shown in FIG. 1, the beam splitter 200 is disposed between the light source module 100 and the scanning module 400. Light emitted by the light source module 100 can pass through the beam splitter and reach the scanning module 400, and the beam splitter 200 can reflect reflected light from the detection position to the imaging module.

In the present disclosure, the specific structure of the beam splitter 200 is not specifically limited. The "guided by the beam splitter" described above will be described in detail below in connection with two implementations of the beam splitter 200.

In a first case, that is, the case shown in FIG. 1, the beam splitter 200 may include a transparent body and a beam splitting film disposed on the transparent body. That is, the beam splitter 200 may be a beam splitting plate or a beam splitting prism.

One of the light source module 100 and the imaging module 800, the beam splitter 200, the scanning module 400 and the flat field objective lens 600 are disposed on a same first straight line L1, an included angle between the beam splitting film and the first straight line L1 is 45°, and the other of the light source module 100 and the imaging module 800 is disposed on a second straight line L2 perpendicular to the first straight line L1.

Which one of the light source module 100 and the imaging module 800 is disposed on the first straight line L1 and which one of the light source module 100 and the imaging module 800 is disposed on the second straight line L2 are determined by a ratio of transmissivity to reflectivity of the beam splitting film.

For example, in the implementation shown in FIG. 1, in order to achieve imaging of the retina, the transmissivity of the beam splitter 200 is smaller than the reflectivity of the beam splitter 200, and preferably, the ratio of transmissivity to reflectivity of the beam splitter may be set to 1:9. In this case, "the detection light is guided by the beam splitter 200 to the scanning module 400" means that the detection light is transmitted through the beam splitter 200 and reaches the scanning module 400, "the reflected light from the detection position can pass through the scanning module 400 and reaches the beam splitter 200 and is guided by the beam splitter 200 to the imaging module 800" means that the reflected light from the detection position can pass through the scanning module 400 and reaches the beam splitter 200, and be reflected by the beam splitter 200 to the imaging module 800.

When the transmissivity of the beam splitter 200 is greater than the reflectivity of the beam splitter 200, the imaging module 800 may be disposed on the first straight line L1, and the light source module 100 may be disposed on the second straight line L2. In this implementation, preferably, the ratio of transmissivity to reflectivity of the beam splitter may be set to 9:1. In this case, "the detection light is guided by the beam splitter 200 to the scanning module 400" means that the detection light is reflected by the beam splitter 200 to the scanning module 400, "the reflected light from the detection position can pass through the scanning module 400 and reaches the beam splitter 200 and is guided by the beam splitter 200 to the imaging module 800" means that the reflected light from the detection position can pass through the scanning module 400 and reaches the beam splitter 200 and reaches the imaging module 800 after being transmitted through the beam splitter 200.

Figure 2A:
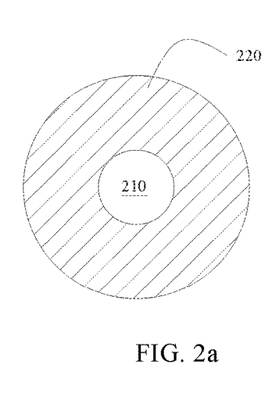
FIG. 2a is a schematic diagram of an implementation of a beam splitter.
Figure 2B:
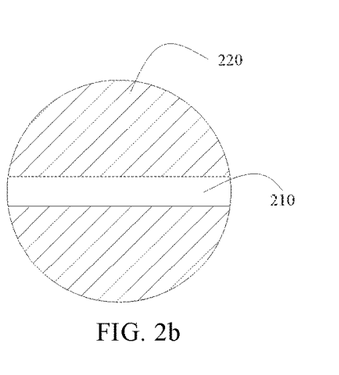
FIG. 2b is a schematic diagram of another implementation of a beam splitter.

In a second case, as shown in FIGS. 2a and 2b, the beam splitter 200 may be a hollow reflector. As shown in FIG. 2, the beam splitter 200 includes a first light reflection portion 220 and a first light transmission portion 210 formed on the first light reflection portion 220. The first light reflection portion 220 has a reflection surface facing the scanning module 400, and reflects light reflected from the fundus to the imaging module 800. In this implementation, the reflection surface of the first light reflection portion 220 faces the scanning module 400, and has an included angle of 45° with respect to the scanning module 400, the light source module 100, the beam splitter 200, the scanning module 400, and the flat field objective lens 600 are arranged on the first straight line L1, and the imaging module 800 is disposed on the second straight line L2 perpendicular to the first straight line L1. The detection light emitted from the light source module 100 can pass through the first light transmission portion 210, and the reflected light back from the detection position can be reflected by the first light reflection portion 220 to the imaging module 800.

The beam splitter 200 shown in FIGS. 2a and 2b can eliminate stray light, making the obtained fundus image clearer.

As shown in FIG. 2a, the light transmission portion 210 may be a circular through hole. The diameter of the light transmission portion 210 is preferably 3 mm, and in this case, the light transmission portion can filter out stray light. The detection light in which the stray light has been filtered out is emitted into the scanning module 400.

Needless to say, the light transmission portion 210 may also be a hole having other shape. For example, the light transmission portion 210 may be a slit having a width of 3 mm as shown in FIG. 2b.

Figure 6:
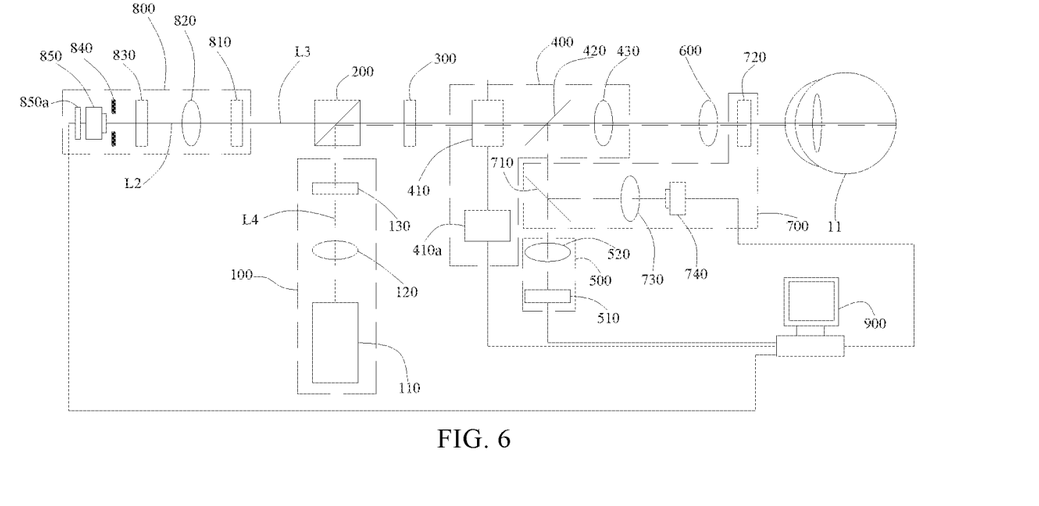
FIG. 6 is a schematic structural diagram of a second implementation of an optical component for retinal imaging provided by the present disclosure.

In the implementation shown in FIG. 6, the beam splitter 200 is disposed between the imaging module 800 and the scanning module 400. In this implementation, the beam splitter 200 includes a second reflection portion and a second transmission portion, and the second reflection portion has a reflection surface facing the scanning module 400. The imaging module 800, the beam splitter 200, the scanning module 400 and the flat field objective lens 600 are arranged on a third straight line L3, and the light source module 100 is disposed on a fourth straight line L4 perpendicular to the third straight line L3 such that the detection light emitted by the light source module 100 can be emitted onto the second light reflection portion, and reflected by the second light reflection portion to the scanning module 400, and reflected light back from the detection position can pass through the second light transmission portion and reaches the imaging module.

In this implementation, the second light transmission portion may be a circular hole or a slit formed on the second light reflection portion. The reflected light back from the detection position can pass through the second light transmission portion.

In this implementation, the reflection surface of the second reflection portion of the beam splitter 200 faces the light source module 100, and has an included angle of 45° with respect to the fourth straight line L4 where the light source module is located.

In the implementation shown in FIG. 6, the beam splitter may also include a transparent body and a beam splitting film disposed on the transparent body.

In the present disclosure, there is no particular limitation on how to move the scanning objective lens 430. As an implementation, the scanning module 400 may include a first guide rail (not shown) extending in a direction coinciding with the central axis of the scanning objective lens 430, and the scanning objective lens 430 is slidably disposed on the first guide rail. There is no particular limitation on how to drive the scanning objective lens 430 to slide on the first guide rail. For example, the scanning objective lens 430 may be driven to slide along the first guide rail by a stepping motor. With the stepping motor, the position of the scanning objective lens 430 can be precisely controlled, so that the defocusing amount of the scanning objective lens 430 can be accurately controlled, which makes the detected image more accurate.

In the present disclosure, there is also no particular requirement on how the flat field objective lens 600 moves. For example, the optical component may include a second guide rail (not shown) extending in the direction coinciding with the central axis of the flat field objective lens 600, and the flat field objective lens 600 is slidably disposed on the second guide rail. Similar to the driving of the scanning objective lens 430, the flat field objective lens 600 may be driven to slide along the second guide rail by a stepping motor.

Preferably, the detection light entering the scanning module 400 is a linear beam, and accordingly, the optical component may further include a first cylindrical lens 300 disposed between the beam splitter 200 and the scanning module 400. The first cylindrical lens 300 can convert the narrow beam transmitted through the beam splitter 200 into linear structured light, and the linear structured light passes through the scanning module 400 and enters a human eye, and forms linear structured light on the retina of the human eye. After being reflected by the retina, the linear structured light entering the fundus carries intensity information of the linear structured light on the retina, backtracks, and is reflected by the beam splitter 200 to the imaging module 800.

In the present disclosure, the first cylindrical lens 300 may be an achromatic cemented cylindrical lens capable of eliminating chromatic aberration in the range of 400 nm to 900 nm. For example, ACY254-050-A from Thorlabs Inc. may be selected as the first cylindrical lens 300.

In the present disclosure, the specific structure of the light source module 100 is not limited. In the implementation shown in FIG. 1, the light source module 100 includes a broadband point light source 110 and a collimating lens 120 that are sequentially arranged. Here, the broadband point light source 110 may be a pigtailed point light source. Light emitted by the broadband point light source 110 becomes a parallel beam after passing through the collimating lens 120.

The layers of the retina have different sensitivities to the spectrum, and different layers of different retinas may be imaged or contrast imaged according to specific needs. For example, in the case of observing the visual cell layer, it is suitable to use near infrared light. In the case of observing blood flowing in a blood vessel, it is suitable to use green light. In the case of observing the pigment epithelial layer, it is suitable to utilize an auto-fluorescence effect of lipofuscin under the excitation of 568 nm. In order to achieve the above functions, the light source module 100 can emit various light descried above.

In the present disclosure, the light source module 100 may include a plurality of point light sources 110 that emit lasers having different wavelengths, respectively, to cooperate with the scanning module and the imaging module to provide light sources for different layers.

In order to simplify the structure of the light source module 100, preferably, the light source module 100 includes a point light source 110, a collimating lens 120, and a first filter group 130 which are sequentially arranged. The point light source 110 is configured to emit a broadband laser having a plurality of wavelengths. The first filter group 130 includes a plurality of first filters, the number of the first filters is equal to the number of the plurality of wavelengths of the laser emitted by the first light source, the first filter is capable of filtering the laser emitted by the point light source to transmit laser having a predetermined wavelength, and each of the first filters may be detachably disposed in an optical path of the optical component. Accordingly, the imaging module 800 includes a second filter group 810 disposed between the beam splitter 200 and the first imaging objective lens 820, the second filter group 810 includes a plurality of second filters, and the plurality of second filters are capable of transmitting fluorescence having different wavelengths, respectively.

Here, "detachably disposed" means that the first filter in the first filter group may be taken out from the optical path, or the first filter may be disposed in the optical path.

Since the point light source 110 emits a broadband laser, a narrowband laser having a corresponding wavelength can be obtained after the broadband laser is filtered by the first filter. The filter has a lower cost than a point source, moreover, the filter is small in size, does not require power, and can be easily mounted in or removed from the optical component.

In the present disclosure, when it is required to obtain an image of the retina, the light emitted by the light source 110 is a point light source, which is collimated into a parallel beam after passing through the collimating lens 120, has a desired spectrum line selected by the desired first filter, and is then split by the beam splitter 200. A portion passing through the beam splitter 200 is converted into a one-dimensional linear beam by the first cylindrical lens 300, reaches the scanning module 400, and is transmitted to the human eye through the scanning module 400.

Figure 3:
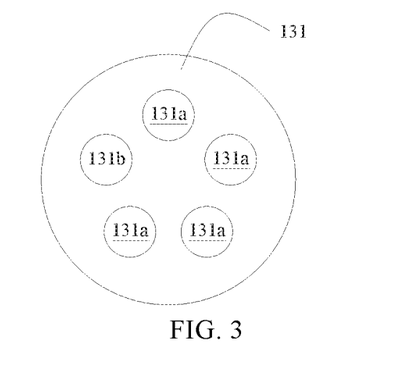
FIG. 3 is a schematic diagram of an implementation of a first turntable.

In the present disclosure, there is no special limitation on how to replace the first filter in the first filter group. As a preferred implementation, as shown in FIG. 3, the light source module includes a first turntable 131. The first turntable 131 is provided with a plurality of first filter through holes 131a in one-to-one correspondence with the plurality of first filters, and each first filter is disposed in the corresponding first filter through hole 131a. By rotating the first turntable, the desired first filter can be placed in the optical path.

Preferably, as shown in FIG. 3, the first turntable 131 may be further provided with a first through hole 131b. No filter is disposed in the first through hole 131b, and light can pass directly through the first through hole 131b. In this implementation, the first filter can be disposed in or removed from the optical path by rotating the turntable without removing the rotary turntable, which facilitates operation of an operator.

Similarly, in the present disclosure, there is no particular limitation on how to replace the second filter in the second filter group. In a preferred implementation, the imaging module includes a second turntable, and the second turntable is provided with a plurality of second filter through holes in one-to-one correspondence with the plurality of the second filters. Each second filter is disposed in the corresponding second filter through hole. By rotating the second turntable, the desired second filter can be placed in the detection optical path.

In order to facilitate the operation of the operator, preferably, similar to the first turntable, a second through hole may be disposed in the second turntable, no filter is disposed in the second through hole, and the light can pass directly through the second through hole.

As a preferred implementation, the point light source includes an argon laser emitter capable of emitting a broadband laser having a central wavelength of 488 nm and a broadband laser having a central wavelength of 514 nm and a semiconductor laser emitter capable of emitting a broadband laser having a central wavelength of 795 nm and a broadband laser having a central wavelength of 830 nm.

The first filter group includes a first filter capable of transmitting a laser having a wavelength of 488 nm, a first filter capable of transmitting a laser having a wavelength of 514 nm, a first filter capable of transmitting a laser having a wavelength of 795 nm, and a first filter capable of transmitting a laser having a wavelength of 830 nm.

The second filter group includes a second filter capable of transmitting fluorescence having a wavelength of 500 nm and a second filter capable of transmitting fluorescence having a wavelength of 810 nm.

In practical applications, the argon laser emitter and the semiconductor laser emitter may be selectively controlled to emit light.

When it is required to perform sodium fluorescein angiography on the fundus, a first filter capable of transmitting a laser having a wavelength of 488 nm and a second filter capable of transmitting fluorescence having a wavelength of 500 nm are disposed in the optical path, so that sodium fluorescein angiography can be realized.

When performing red-free imaging on the retina, a first filter capable of transmitting a laser having a wavelength of 514 nm may be disposed in the optical path, and all of the second filters may be taken out from the optical path, so that red-free imaging on the retina can be realized.

When it is required to perform indocyanine green angiography on the fundus, a first filter capable of transmitting a laser having a wavelength of 795 nm and a second filter capable of transmitting fluorescence having a wavelength of 810 nm are disposed in the optical path to achieve indocyanine green angiography.

When it is required to perform infrared imaging on the retina, a first filter capable of transmitting a laser having a wavelength of 830 nm is disposed in the optical path, and the second filter is taken out from the optical path, to realize infrared imaging of the retina.

As a preferred implementation, as shown in FIG. 1, the scanning module 400 may further include a galvanometer scanner 410 and a first dichroic beamsplitter 420. The first dichroic beamsplitter 420 and the scanning objective lens 430 are sequentially arranged between the galvanometer scanner 410 and the flat field objective lens 600.

As shown in the figures, the included angle between the beam splitting film of the first dichroic beamsplitter 420 and the first straight line L1 may be 45°.

In order to achieve imaging of different regions of the retina, preferably, the optical component may also include a test-object module 500. As shown in FIG. 1, the test-object module 500 includes a light-emitting array 510 and a third imaging objective lens 520. The light-emitting array includes a plurality of light-emitting elements (the light-emitting elements may be LEDs) that can be controlled independently, and light emitted by any one of the light-emitting elements can be incident into the third imaging objective lens 520, and the third imaging objective lens 520 focuses the incident light. The focused light is directed toward the first dichroic beamsplitter 420 and reflected by the first dichroic beamsplitter 420 to the flat field objective lens 600, and finally to the corresponding region of the fundus of the human eye 11.

In this implementation, by controlling the light-emitting elements at different positions of the light-emitting array 510 to emit light, different regions on the retina of the human eye 11 can be illuminated, so that imaging of different regions of the retina can be achieved.

In the present disclosure, how to drive each of the light-emitting elements of the light-emitting array 510 to emit light is not particularly limited. For example, the light-emitting array 510 may be coupled to a main control computer 900 through any data interface such as the USB interface, the Bluetooth, the network cable interface, a serial port, a parallel port, or the like. The main control computer 900 controls light emission of different light-emitting elements on the light-emitting array 510.

The central axis of the third imaging objective lens 520 of the test-object module 500 is perpendicular to the first straight line L1.

In order to realize real-time detection of the pupil of the human eye, facilitate system debugging, and facilitate imaging detection of the subject, preferably, the optical component further includes a pupil detection module 700, and the pupil detection module 700 includes a second dichroic beamsplitter 710, an annular light source 720 and a second imaging objective lens 730.

The annular light source 720 is disposed between the flat field objective lens 600 and the detection position, and is capable of emitting light toward the detection position.

The second dichroic beamsplitter 710 is disposed between the first dichroic beamsplitter 420 of the scanning module 400 and the third objective lens 520, and an included angle between the beam splitting film of the second dichroic beamsplitter 710 and the central axis of the third objective lens 520 is 45°. The reflected light from the detection position can be irradiated to the first dichroic beamsplitter 420 after passing through a hollow portion of the annular light source 720, and reflected by the first dichroic beamsplitter 420 to the second dichroic beamsplitter 710, and the second dichroic beamsplitter 710 can reflect the light reflected by the first dichroic beamsplitter 420 to the second imaging objective lens 730. An image of the pupil of the human eye can be obtained through the second imaging objective lens 730. The central axis of the second imaging objective lens 730 is perpendicular to the central axis of the third imaging objective lens 520.

The annular light source 720 may be an annular LED tube with a circular through hole in the middle. Light emitted by the annular light source illuminates the cornea of the human eye, the cornea reflects an annular beam emitted by the annular light source, the reflected light directly passes through the through hole in the middle of the annular light source 720, then is reflected by the first dichroic beamsplitter 420 to the second dichroic beamsplitter 710, focused by the second imaging objective lens 730 after being reflected by the second dichroic beamsplitter 710 and enters into an area array photodetector 740. The area array photodetector 740 converts a light intensity signal into an electrical signal and output the electrical signal directly to the main control computer 900, so that the computer 900 obtains an image of the pupil of the human eye, achieves real-time monitoring of the pupil, achieves functions of alignment and positioning of the system optical imaging. Moreover, the main control computer 900 can achieve image storage, image processing and analysis, file processing, etc.

In the present disclosure, the specific structure of the annular light source is not particularly limited. For example, the annular light source may be an annular light source formed by arranging a plurality of LEDs. It should be noted that the annular light source is hollow in the middle, so as to allow the detection light and the reflected light to pass therethrough.

Preferably, the pupil detection module 700 may further include an area array photodetector 740, which can detect light from the second imaging objective lens 730 to form an image.

Preferably, the imaging module 800 further includes a second cylindrical lens 830, a slit aperture 840, and a linear array photodetector 850 sequentially arranged at a light exiting side of the first imaging objective lens 820.

The light reflected by the beam splitter 200 passes through the first imaging objective lens 820 to match the magnification, is focused by the second cylindrical lens 830 into a linear beam, passes through the slit aperture 840 and reaches the linear array photodetector 850 to obtain continuous light intensity information of the position of the retina illuminated by linear beam.

The second cylindrical lens 830 can improve the utilization of light and reduce energy loss. The slit aperture 840 can filter out stray light, making the resulting image clearer.

Preferably, the slit aperture has a slit whose width is equal to the Airy disk diameter of the imaging objective lens, so that stray light out of the focal plane of the human retina can be completely filtered out, thereby ensuring high resolution of the confocal imaging.

The galvanometer scanner 410 performs one-dimensional scanning on the incident linear structured light, which is then matched by the scanning objective lens 430, enters the human eye after being transformed by the flat field objective lens 600, and is focused by the optical system of the human eye to form a linear structured beam on the retina, the fundus of the human eye scatters the incident light, the scattered light includes an imaging beam carrying light intensity information of the retina of the human eye, and the imaging beam is reflected from the retina of the human eye and is emitted out. Subsequently, the imaging beam reflected by the human eye is converted into a flat field beam by the flat field objective lens 600 and backtracks to the beam splitter 200, and the beam splitter 200 reflects the imaging beam to the imaging module 800.

Since the retina is a curved structure with a large curvature, the imaging beam reflected by the retina has a large distortion aberration. Therefore, the imaging beam also has a curved shape, and by using the flat field objective lens 600 in combination with the optical system parameters and the retinal structure of the human eye, the imaging beam reflected by the curved retina surface can be converted into a flat field beam, eliminating the effect of distortion.

In the implementation shown in FIG. 1, the imaging module 800 includes a second filter group 810, a first imaging objective lens 820, a second cylindrical lens 830, a slit aperture 840, and a linear array photodetector 850 which are sequentially arranged. The imaging beam is focused by the first imaging objective lens 820 after passing through the second filter in the second filter group 810 which selects a desired spectrum line of the imaging beam, is then converted by the second cylindrical lens 830 back into a linear beam, and enters the linear array photodetector 850 after passing through the slit aperture 840 which filters out stray light.

In the optical component provided by the present disclosure, the image quality in different fields of view of the retina is used as an evaluation index, so that the illumination of the linear structured beam on the retina of the human eye reaches diffraction limit.

As another aspect of the present disclosure, there is provided a retinal imaging device including an optical component and a processor. The optical component is the above optical component provided by the present disclosure, and the processor includes an image generation module configured to generate a corresponding image based on light emitted from the imaging module.

As described above, since the scanning objective lens 430 can generate different defocusing amounts, different layers on the retina can be imaged, and a more comprehensive examination of the retina can be achieved. Moreover, the flat field objective lens 600 can generate different defocusing amounts, the refractive error of the human eye can thus be compensated for, so that clear fundus images can be obtained for different patients.

In the present disclosure, the processor may include a main control computer 900.

In a case where the optical component includes the linear array photodetector 850 and the galvanometer scanner 410, the image generation module may include an image acquisition board 850a and a function generator board 410a. An input end of the image acquisition board 850a is coupled to an output end of the linear array photodetector 850 and configured to generate a corresponding image based on the electrical signal generated by the linear array photodetector 850. The function generator board 410a is coupled to the galvanometer scanner 410 and the main control computer 900, respectively, and configured to drive the galvanometer scanner 410.

In the present disclosure, the main control computer 900 is mainly configured to output various control commands to implement functions such as reconstruction, display, storage, processing and analysis of image and file processing.

Needless to say, in a case where the linear array photodetector 850 is a network cable interface, the image generation module may not include the image acquisition board, and a corresponding image is generated based on the electrical signal output by the linear array photodetector 850.

In a case where the optical component includes the pupil detection module 700, the image generation module is further configured to generate an image obtained by the pupil detection module 700. In the implementation shown in FIG. 1, the main control computer 900 is coupled to the output end of the area array photodetector 740.

Figure 4:
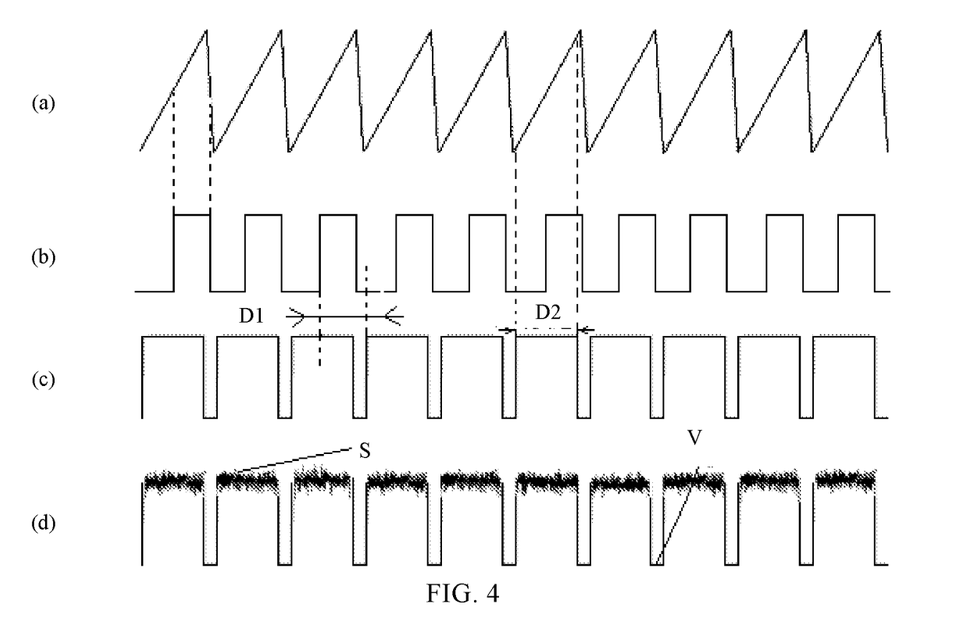
FIG. 4(a) is a timing diagram of a scan driving signal.
FIG. 4(b) is a timing diagram of a scan synchronization signal.
FIG. 4(c) is a timing diagram of a frame synchronization signal.
FIG. 4(d) is a timing diagram of a signal of a linear array photodetector modulated by frame synchronization.

The working principle of the retinal imaging device provided by the present disclosure will be described below with reference to FIGS. 1 and 4.

In the implementation shown in FIG. 1, the optical component includes a light source module 100, a beam splitter 200, a first cylindrical lens 300, a scanning module 400, a test-object module 500, a flat field objective lens 600, a pupil detection module 700, and an imaging module 800.

The light source module 100 includes a point light source 110, a collimating lens 120, and a first filter group. The point light source 110 includes an argon laser emitter capable of emitting a laser having a central wavelength of 488 nm and a laser having a central wavelength of 514 nm, and a semiconductor laser emitter capable of emitting a laser having a central wavelength of 795 nm and a laser having a central wavelength of 830 nm.

The first filter group includes four narrowband filters, which are a first filter capable of transmitting light having a wavelength of 488 nm, a first filter capable of transmitting light having a wavelength of 514 nm, a first filter capable of transmitting light having a wavelength of 795 nm, and a first filter capable of transmitting light having a wavelength of 830 nm, respectively.

The collimating lens 120 is an achromatic doublet lens capable of eliminating chromatic aberration of light in the range of 400 nm to 900 nm, and the collimating lens 120 has a focal length of 30 mm.

The beam splitter 200 is a beam splitter including a light transmission portion and a light reflection portion shown in FIG. 2, and the light transmission portion has a diameter of 3 mm.

The first cylindrical lens 300 is an achromatic cemented cylindrical lens and can eliminate chromatic aberration of light in the range of 400 nm to 900 nm. In the present disclosure, ACY254-050-A from Thorlabs Inc. is used.

The scanning module 400 includes a galvanometer scanner 410, a first dichroic beamsplitter 420, and a scanning objective lens 430 which are sequentially arranged. The galvanometer scanner 410 is a reflective galvanometer scanner. In the present disclosure, the galvanometer scanner of model 6210H from Cambridge Technology Inc. is used, and has an effective optical aperture of 3 mm. The first dichroic beamsplitter 420 is a spectral beam splitter. The scanning objective lens 430 is an achromatic cemented lens. In the present disclosure, a 400 nm to 900 nm achromatic cemented lens is used, and has a focal length of 50 mm.

The flat field objective lens 600 eliminates the non-flat field distortion of the curved retinal surface. In the present disclosure, a flat field objective lens of VOLK 66D slit lamp lens from Volk Inc. is used.

The pupil detection module 700 includes a second dichroic beamsplitter 710, an annular light source 720, a second imaging objective lens 730, and an area array photodetector 740.

The second dichroic beamsplitter 710 is a beam splitting plate, and the beam splitting film of the second dichroic beamsplitter 710 is designed based on the spectral line of light emitted by the test-object module 500 and the spectral line of the beam emitted by the annular light source 720.

The circular through hole in the middle of the annular light source 720 has a diameter of 10 mm.

The second imaging objective lens 730 is an achromatic doublet lens. In the present disclosure, an achromatic doublet lens that can eliminate achromatic aberration of light in the range 400 nm to 900 nm is employed, and has a focal length of 80 mm.

The area array photodetector 740 may be an area array charge coupled device, or an area array complementary metal oxide semiconductor array, or an area array photodiode array. In an embodiment, an area array charge coupled camera from Basler Inc., Germany is used, the model may be daA1920-30 um, which has 1920×1080 pixels, is monochrome, and has a frame rate up to 30 frames per second.

The test-object module 500 includes a light-emitting array 510 and a third imaging objective lens 520. The light-emitting array 510 is an 8×8 LED array, and a center-to-center spacing between two adjacent LEDs is 2 mm. The third imaging objective lens 520 is an achromatic doublet lens having a focal length of 100 mm.

The imaging module 800 includes a second filter group 810, a first imaging objective lens 820, a second cylindrical lens 830, a slit aperture 840, and a linear array photodetector 850. The second filter group includes a second filter that can transmit light having a wavelength of 500 nm and a second filter that can transmit light having a wavelength of 810 nm.

The first imaging objective lens 820 is an achromatic doublet lens. In the present disclosure, an achromatic doublet lens that can eliminate achromatic aberration in the range 400 nm to 900 nm is employed, and has a focal length of 100 mm.

The second cylindrical lens 830 employs an achromatic cylindrical lens for achromatic aberration in the range of 400 nm to 900 nm. In an embodiment, a ACY254-050-A cylindrical lens from Thorlabs Inc. is used.

The slit aperture 840 is an adjustable slit aperture. In an embodiment, APAS80-1A from ZOLIX INSTRUMENTS CO., LTD is used, and its position is conjugate with the retinal plane of the fundus.

The linear array photodetector 850 is a linear array charge coupled device, or a linear array complementary metal oxide semiconductor array, or a linear array photodiode array. In an embodiment, a line CCD from BASLER Inc. is adopted, and the model is spL2048-140 km, which has 2*2048 pixels, and the pixel size is 10 μm×10 μm. The linear array photodetector 850 converts continuous light intensity signals into analog electric signals, the galvanometer scanner 410 generates a synchronous voltage, and the analog electric signals and the synchronous voltage are sent together to the control processor formed by the function generator board 410a and the image acquisition board 850a. The image acquisition board 850a firstly modulates the synchronous voltage to obtain a frame synchronization signal, and then samples the analog electrical signals output by the linear array photodetector 850 according to the frame synchronization signal, determines a line on the retina to which the intensity information at a time point corresponds, and finally restores real-time intensity information of a rectangular area on the retina on the main control computer 900. The details are as follows.

As shown in FIG. 4(a), a scan driving signal of the galvanometer scanner 410 is a sawtooth wave signal, which needs to be converted into a frame synchronization signal. In the present embodiment, a comparator may be used to convert the scan driving signal, which is a sawtooth waveform, into a frame synchronization signal. Since the amplitude of the scan driving signal is adjustable according to the requirements of the scanning area, if the scan driving signal is directly compared with a fixed level value to obtain the frame synchronization signal, the frame synchronization signal thus obtained is amplitude-dependent, Every time the amplitude of the scan driving signal is adjusted, it is necessary to provide a new comparison level, which results in poor operation. Therefore, as a design, the driving signal is compared with the zero level (as shown in FIG. 4(b)) to obtain the scan synchronization signal (as shown in FIG. 4(c)), and this process is independent of the amplitude of the scan driving signal. Further, the scan synchronization signal may be shifted and delayed to obtain a stable frame synchronization signal (as shown in FIG. 4(c)) as practically required.

In FIG. 4(c), D1 represents a delay, and the pulse width of the frame synchronization signal is represented by D2. In FIG. 4(d), S represents the signal detected by the linear array photodetector, and V represents the level reference, which is a zero level here.

As shown in FIG. 1, the scan driving signal output from the galvanometer scanner 410 needs to be modulated by the function generator board 410a to obtain a frame synchronization signal; the signal output from the linear array photodetector 850 needs to be modulated using the frame synchronization signal, then input to the image acquisition board 850a for sampling to reconstruct the image signal, and output to the main control computer 900 for image acquisition and display, image storage, image processing and analysis, file processing, and the like.

The function generator board 410a may use a function generator board of model NI PCI-6221 from National Instruments Inc. USA.

The image acquisition board 850a may use an image acquisition board of model NI PCI-5122 from National Instruments Inc. USA.

FIG. 5 illustrates a method of imaging a retina of a subject using the retinal imaging device shown in FIG. 1.

As shown in FIG. 1, a human eye 11 to be imaged is observed. First, the device can perform a line scan imaging function on the retina of the human eye 11, and has at least four imaging functions as follows.

After manually injecting a fluorescent sodium dye into a subject, the argon laser emitter is turned on, the first filter group is set through the first turntable, and the first filter capable of transmitting the laser having a wavelength of 488 nm is selected from the first filter group. The laser beam illuminates a retina after passing through the optical component, so as to excite the fluorescent sodium dye at the fundus. At the same time, the second filter group is set through the second turntable, and the second filter capable of transmitting fluorescence having a wavelength of 500 nm is selected from the second filter group to realize sodium fluorescein angiography on the retina.

The argon laser emitter is turned on, the first filter group is set through the first turntable, and the first filter capable of transmitting a laser having a wavelength of 514 nm is selected. The laser beam illuminates the fundus after passing through the optical component. At the same time, the second filter group is set through the second turntable, and the second filter is taken out from the optical path to allow the imaging beam to pass directly, so that the red light-free imaging of the retina is realized.

After manually injecting the indocyanine green dye into a subject, the semiconductor laser emitter is turned on, the first filter group is set through the first turntable, and the first filter capable of transmitting a laser having a wavelength of 795 nm is selected from the first filter group. The laser beam illuminates the retina after passing through the optical component, so as to excite the indocyanine green dye at the fundus. At the same time, the second filter group is set through the second turntable, and the second filter capable of transmitting the fluorescence having a wavelength of 810 nm is selected from the second filter group to achieve the indocyanine green angiography.

The semiconductor laser emitter is turned on, the first filter group is set through the first turntable, and the first filter capable of transmitting a laser having a wavelength of 830 nm is selected. The laser beam illuminates the fundus after passing through the optical component. At the same time, the second filter group is set through the second turntable, and the second filter is taken out from the optical path to allow the imaging light beam to directly pass to achieve infrared imaging of the retina.

A specific operation process of the present disclosure is shown in FIG. 5.

The machine is turned on, system hardware is checked, the subject gets prepared accordingly, and a fluorescent dye needs to be injected manually if fluorescence imaging needs to be performed.

S1 includes: placing the head of the subject on a head frame, turning on the annular light source 720, adjusting the position of the head frame such that light emitted by the annular light source 720 illuminates a cornea of the human eye 11.

S2 includes: focusing light reflected back from the cornea of the human eye 11 and traveling along the optical path into the area array photodetector 740 to realize real-time monitoring of the pupil of the human eye 11. When the pupil is located in the middle of the imaging field, it is indicated that the human eye has been adjusted to a center position of the optical path.

S3 includes: turning on the point light source 110, turning on the galvanometer scanner 410, turning on the control processor formed by the function generator board 410a, the image acquisition board 850a, and the main control computer 900, and for the defocusing amount of a refractive error of the human eye 11, driving the flat field objective lens 600 to generate a defocusing compensation amount along the second guide rail to compensate for the defocusing amount of the human eye.

S4 includes: selecting a combination of the first filter and the second filter according to the imaging function, letting the subject keep the eye stable, and starting a data acquisition program for video acquisition.

S5 includes: turning on a corresponding LED of the light-emitting array 510 by the control processor according to an area of the retina to be imaged, to illuminate the area of the retina.

S6 includes: causing the scanning objective lens 430 to generate defocus along the first guide rail to illuminate layers of the retina at different depths, thereby acquiring a three-dimensional image of the layers of the retina at different depths.

It could be understood that the above embodiments are merely exemplary embodiments employed to explain the principle of the present disclosure, but the present disclosure is not limited thereto. Various modifications and improvements can be made by those skilled in the art without departing from the spirit and scope of the present disclosure. These modifications and improvements are also considered to be within the protection scope of the present disclosure.

The invention claimed is:

1. An optical component for retinal imaging comprising: a light source module, a beam splitter, an imaging module, a scanning module, and a flat field objective lens, wherein the flat field objective lens is disposed between the scanning module and a detection position, the light source module is configured to emit, to the beam splitter, a detection light for illuminating a fundus, the detection light being guided by the beam splitter to the scanning module and emitted to the detection position through the scanning module and the flat field objective lens, reflected light from the detection position is able to pass through the scanning module and reaches the beam splitter, and is guided by the beam splitter to the imaging module, wherein the scanning module comprises a scanning objective lens reciprocally movable along a central axis of the scanning objective lens, and the flat field objective lens is reciprocally movable along a central axis of the flat field objective lens, wherein the light source module comprises a broadband point light source, a collimating lens and a first filter group which are arranged in sequence, the broadband point light source is configured to emit broadband lasers having a plurality of wavelengths, the first filter group comprises a plurality of first filters, a number of the first filters being equal to a number of the plurality of wavelengths of the lasers emitted by the broadband point light source, the first filters are capable of filtering the lasers emitted from the broadband point light source into lasers each having a predetermined wavelength, and each of the plurality of first filters is detachably disposed in an optical path of the optical component; and the imaging module comprises a first imaging objective lens and a second filter group, the second filter group is disposed between the beam splitter and the first imaging objective lens such that light reflected by the beam splitter enters the first imaging objective lens after passing through the second filter group, the second filter group comprises a plurality of second filters, and the plurality of the second filters are capable of transmitting fluorescence having different wavelengths, respectively.

2. The optical component of claim 1, wherein the scanning module comprises a first guide rail extending in a direction coinciding with the central axis of the scanning objective lens, and the scanning objective lens is slidably disposed on the first guide rail.

3. The optical component of claim 1, wherein the optical component comprises a second guide rail extending in a direction coinciding with the central axis of the flat field objective lens, and the flat field objective lens is slidably disposed on the second guide rail.

4. The optical component of claim 1, further comprising a first cylindrical lens disposed between the beam splitter and the scanning module and configured to convert a beam passing through the beam splitter into a linear beam and cause the linear beam to be emitted to the scanning module.

5. The optical component of claim 1, wherein the light source module comprises a first turntable, the first turntable is provided with a plurality of first filter through holes in one-to-one correspondence with the plurality of first filters, and each of the plurality of first filters is disposed in a corresponding one of the plurality of first filter through holes.

6. The optical component of claim 1, wherein the imaging module comprises a second turntable, the second turntable is provided with a plurality of second filter through holes in one-to-one correspondence with the plurality of second filters, and each of the plurality of second filters is disposed in a corresponding one of the plurality of second filter through holes.

7. The optical component of claim 1, wherein the broadband point light source comprises an argon laser emitter and a semiconductor laser emitter, the argon laser emitter is capable of emitting a broadband laser having a central wavelength of 488 nm and a broadband laser having a central wavelength of 514 nm, and the semiconductor laser emitter is capable of emitting a broadband laser having a central wavelength of 795 nm and a broadband laser having a central wavelength of 830 nm;

the first filter group comprises a first filter capable of transmitting a laser having a wavelength of 488 nm, a first filter capable of transmitting a laser having a wavelength of 514 nm, a first filter capable of transmitting a laser having a wavelength of 795 nm, and a first filter capable of transmitting a laser having a wavelength of 830 nm; and the second filter group comprises a second filter capable of transmitting fluorescence having a wavelength of 500 nm and a second filter capable of transmitting fluorescence having a wavelength of 810 nm.

8. The optical component of claim 1, wherein the scanning module further comprises a galvanometer scanner and a first dichroic beamsplitter, the first dichroic beamsplitter and the scanning objective lens are sequentially arranged between the galvanometer scanner and the flat field objective lens; and the optical component further comprises a test-object module comprising a light-emitting array and a third imaging objective lens, the light-emitting array comprises a plurality of light-emitting elements each being independently controllable, light emitted by any one of the light-emitting elements is able to be emitted into the third imaging objective lens, directed to the first dichroic beamsplitter after being focused by the third imaging objective lens and reflected by the first dichroic beamsplitter to the flat field objective lens.

9. The optical component of claim 8, further comprising a pupil detection module, wherein the pupil detection module comprises a second dichroic beamsplitter, an annular light source and a second imaging objective lens, and the annular light source has a hollow portion capable of transmitting light, and the second dichroic beamsplitter is disposed between the first dichroic beamsplitter and the third imaging objective lens such that light passing through the third imaging objective lens is able to pass through the second dichroic beamsplitter, the annular light source is disposed between the flat field objective lens and the detection position, the annular light source is able to emit light toward the detection position, light emitted by the light source module is able to pass through the hollow portion of the annular light source, reflected light from the detection position is able to be emitted to the first dichroic beamsplitter after passing through the hollow portion of the annular light source and reflected by the first dichroic beamsplitter to the second dichroic beamsplitter, and the second dichroic beamsplitter is able to reflect the light reflected by the first dichroic beamsplitter to the second imaging objective lens.

10. The optical component of claim 9, wherein the pupil detection module further comprises an area array photodetector configured to receive light emitted from the second imaging objective lens.

11. The optical component of claim 9, a transmissivity of the second dichroic beamsplitter is smaller than a reflectivity of the second dichroic beamsplitter.

12. A retina imaging device, comprising an optical component and a processor, wherein the optical component is the optical component of claim 9, the processor comprises an image generation module configured to generate a corresponding image according to the light emitted from the imaging module, and the image generation module is further configured to generate a corresponding image according to light emitted from the second imaging objective lens.

13. The optical component of claim 1, wherein the imaging module further comprises a second cylindrical lens, a slit aperture and a linear array photodetector which are arranged in sequence at a light exiting side of the first imaging objective lens, wherein the slit aperture, the light source module and the detection position are at conjugate positions.

14. The optical component of claim 13, wherein the slit aperture has a slit whose width is equal to Airy disk diameter of the first imaging objective lens.

15. The optical component of claim 1, wherein the beam splitter is disposed between the light source module and the scanning module such that light emitted by the light source module is able to pass through the beam splitter and reach the scanning module, the beam splitter is able to reflect reflected light from the detection position to the imaging module, the scanning module and the flat field objective lens are arranged on a first straight line, the imaging module is disposed on a second straight line perpendicular to the first straight line such that detection light emitted by the light source module is able to pass through the beam splitter, and reflected light from the detection position is able to be reflected by the beam splitter to the imaging module.

16. The optical component of claim 15, wherein the beam splitter comprises a first light reflection portion and a first light transmission portion formed on the first light reflection portion, the first light reflection portion has a reflection surface facing the scanning module, the detection light emitted by the light source module is able to pass through the first light transmission portion, and the reflected light from the detection position is able to be reflected by the first light reflection portion to the imaging module.

17. The optical component of claim 1, wherein the beam splitter is disposed between the imaging module and the scanning module, the imaging module, the beam splitter, the scanning module and the flat field objective lens are arranged on a third straight line, the light source module is disposed on a fourth straight line perpendicular to the third straight line such that detection light emitted by the light source module is able to be emitted onto the beam splitter and reflected by the beam splitter to the scanning module, and reflected light from the detection position is able to pass through the beam splitter and reach the imaging module.

18. The optical component of claim 17, wherein the beam splitter comprises a second light reflection portion and a second light transmission portion, the second light reflection portion has a reflection surface facing the scanning module, the detection light emitted by the light source module is able to be emitted onto the second light reflection portion and reflected by the second light reflection portion to the scanning module, and the reflected light from the detection position is able to pass through the second light transmission portion and reach the imaging module.

19. A retina imaging device, comprising an optical component and a processor, the optical component is the optical component of claim 1, and the processor comprises an image generation module configured to generate a corresponding image according to the light emitted from the imaging module.

* * * * *